United States Patent [19]

Stahlman

[11] 3,964,166
[45] June 22, 1976

[54] DENTAL PROPHYLAXIS IMPLEMENT
[75] Inventor: Donald B. Stahlman, Indianapolis, Ind.
[73] Assignee: Mynol, Inc., Broomall, Pa.
[22] Filed: Oct. 21, 1974
[21] Appl. No.: 516,399

[52] U.S. Cl. .................................................. 32/59
[51] Int. Cl.² .......................................... A61C 3/06
[58] Field of Search ............................ 32/59, 2, 58

[56] References Cited
UNITED STATES PATENTS
3,599,333  8/1971  Muhler ................................. 32/59
3,618,213  11/1971  Shepherd .......................... 128/136

Primary Examiner—Robert Peshock
Attorney, Agent, or Firm—Joseph G. Denny, III; Peter J. Patane

[57] ABSTRACT

A resilient dental prophylaxis cup comprising an anticariogenic fluoride agent, up to about 25 per cent (by weight) of a water-soluble thermoplastic polymer material and/or up to about 15 per cent (by weight) of a molecular sieve material, whereby the release of the fluoride ions and the uptake of the fluoride ions by the enamel of the teeth are both increased, providing better protection for the enamel of the teeth against dental caries.

60 Claims, No Drawings

DENTAL PROPHYLAXIS IMPLEMENT

BACKGROUND OF THE INVENTION

This invention relates to dental prophylaxis cups of resilient material having incorporated therein an anticariogenic agent as described in U.S. Pat. No. 3,599,333 issued to Joseph C. Muhler, dated Aug. 17, 1971, and assigned to the Indiana University Foundation.

U.S. Pat. No. 3,599,333 describes the prior art and also describes the use of dental prophylaxis cups (hereinafter referred to as "prophy cups," according to customary usage). Briefly, dentists and hygienists employ prophy cups with a dentifrice or prophylaxis paste during the prophylaxis procedure to clean teeth (by removing dental plaque, calculus, acquired pellicle, and/or other exogenous accumulations) and to maintain or impart a high luster on the enamel and dentin surfaces treated. Depending upon the caries susceptibility and the patient's individual needs, the cleaning treatment, in addition, frequently includes an anticariogenic fluoride and/or stannous ion-containing agent which may be included in the prophy cup and/or the dentifrice or prophylaxis paste.

For example, the aforementioned U.S. Pat. No. 3,599,333 describes prophy cups which incorporate part or all of the anticariogenic fluoride-containing agent in the resilient material from which the prophy cups are made.

The anticariogenic fluoride and/or stannous ion-containing agent is intended to provide a topical source of fluoride ions for incorporation into the tooth enamel (1) to replenish the fluoride in the outer enamel layer since the cleaning procedure removes by abrasion the superficial enamel containing the highest concentration of fluoride; (2) to increase the enamel fluoride content above that contained in the enamel prior to the treatment and thereby imparting a higher resistance to dental caries; and (3) to decrease the acid dissolution rate of the tooth enamel upon acute and chronic exposure to the organic acids produced by the colonized bacterial flora common to the oral cavity. To enable the encapsulated anticariogenic fluoride and/or stannous ioncontaining agent to cause the desired effects, it must be adequately released from the resilient material and in a state readily available for interaction with the tooth enamel, all of which has been achieved by this invention.

An object of this invention is to provide an improved dental prophylactic cup which is therapeutically safe (i.e., nontoxic or injurious under the conditions of recommended usage) and effective with regard to rapid and high fluoride and/or stannous ion releasing ability so as to enable a highly significant increase in the enamel fluoride content during a routine dental prophylaxis.

Another object of the invention is to cause and promote the continual and constant release of the anticariogenic agent or agents from the resilient material of the prophylaxis cup.

A further object is to provide a dental prophylaxis cup which reduces the solubility rate of the tooth enamel when exposed to organic acids common to the oral cavity (e.g., acetic acid) thereby increasing the resistance of the tooth enamel to acid related etiological factors which pertain to the dental caries process.

Another object is to provide a prophylaxis cup which will increase the enamel fluoride content as well as the resistance of the tooth enamel to organic acids when used in conjunction with a compatible, fluoride-containing prophylaxis paste to an extent greater than that attainable when the same fluoride-containing prophylaxis paste is not administered with the present invention.

A further object is to provide a dental prophylaxis cup having a pH range between 3.0 and 5.0 at its applicator margins during the prophylaxis procedure, thereby increasing the probability that the simultaneously released fluoride and/or stannous ions will be incorporated immediately into the tooth enamel.

A related object is to hold the cleaning, polishing and anticariogenic materials in better contact with the tooth surface and to avoid excessive splattering thereof during the prophylaxis treatment.

A still further related object of this invention is to reduce the activity of any calcium ions which may be present and yet another object is to protect the resilient material from oxidation and other deterioration.

Another object of this invention is to provide compatible ingredients in a formulation, possessing good molding and thermoplastic characteristics, and which will form a uniform cup body having a strong weld-line and preferably, the ability to retain a screw shank.

Still another object of my invention is to provide a dental prophylaxis cup having the physical and handling properties which will enable the operator to administer a satisfactory prophylaxis. This requires that the prophy cup will not break down (wear) to an excessive extent so as to become unusable prior to the completion of one prophylaxis. In addition, it requires the implement to have a moderate stiffness, yet high resilience, and the ability to clean and polish rapidly the hard dental tissues wth minimal abrasion.

Another object is to provide a means for applying stannous ions to the hard dental tissues without the objectionable features (e.g., strong, bitter metallic taste, gagging, nausea, and profuse salivation during and following the application period) sometimes experienced by patients who have received topical applications of prophylaxis systems containing high concentrations (2–10 percent) of stannous fluoride.

SUMMARY OF THE INVENTION

The present invention provides a dental prophylaxis implement (a prophy cup) comprising a generally cylindrical unitary body formed of resilient material provided with a mounting means at its upper end portion for attachment to a conventional dental hand piece. The bottom end portion of the unitary body is hollowed so as to provide a cavity into which a charge of dental prophylaxis paste or the like may be placed.

The prophy cup incorporates up to about 30 percent by weight of an anticariogenic agent, such as an agent containing fluoride and/or stannous ions, in the resilient material from which the unitary body is formed.

Also, the prophy cup may incorporate up to 50 percent of a dental polishing and cleaning agent.

The prophy cup also incorporates as additives up to 25 percent of a water-soluble thermoplastic polymer in the resilient material and/or up to 15 percent of a finely divided molecular sieve. With these additives significantly increased amounts of fluoride and heavy metal ions, such as the stannous ions, are incorporated into the dental enamel. The molecular sieve, in addition, affords some protection from deterioration of the resilient material on storage as well as in use. Further, it was found that the pliability, resiliency and toughness of the plastic base was advantageously increased by the addition of the molecular sieve. This was unexpected since powdered fillers tend to stiffen and decrease the elastic memory of resilient materials. This property of the molecular sieve thus advantageously serves to counteract those undesirable physical properties attributable and heretofore unavoidable with the incorporation of water-soluble thermoplastic polymers and strengthening agents.

The water-soluble polymers have a further advantage in that when they are released from the resilient base material of the prophy cup, they form a gelatinous mass of cleaning, polishing and anticariogenic materials which better hold or cling to the surface of the tooth being treated and thereby minimize spattering and waste.

The presence of the gelatinous mass clinging to the teeth makes for a more efficient cleaning, i.e., less harsh abrasives are required to achieve the degree of cleaning necessary for clinical acceptance.

Furthermore, the frictional heat normally developed in a prophylaxis aids the release of the water-soluble polymer, since many types of the latter, e.g., hydroxypropyl cellulose, crystallize at temperatures about 40°C., thereby fostering or increasing the breakdown of the cup and the release of the heavy metal ions and the fluoride ions. This breakdown of the cup serves also as a visual aid to avoid excessive pressure and heat on the teeth which might damage the pulp of the teeth.

Further, the water-soluble polymer reacts with the aqueous saliva system and with such solvents as glycerin and propylene glycol, often present in prophy pastes, whereby the cup becomes softer and more pliable and more adaptable to the contours of the tooth.

DETAILED DESCRIPTION OF THE PREFERRED EMBODIMENTS

This invention provides a dental prophylaxis implement adapted for removable mounting on a dental hand piece and comprising a unitary body formed of resilient material, the body having at least one applicator portion capable of performing a dental prophylaxis, and the resilient material from which the unitary body is formed having incorporated therein up to about 30 percent (by weight) of at least one anticariogenic agent, preferably a fluoride, and up to about 25 percent (by weight) of a water-soluble, preferably thermoplastic, polymer and/or up to about 15 percent (by weight) of a molecular sieve.

The resilient material may be natural or synthetic rubber or plastics such as polyamides (e.g., nylon), polystyrenes, polyolefins, including polyethylene and polypropylene, cellulosics and acrylics which have suitable resilience, flexibility and compatibility with anticariogenic and water-soluble agents under the conditions of manufacture and use. Butadiene-styrene block co-polymers, for example, the styrene-butadiene-styrene and styrene-isoprene-styrene co-polymers, both available from the Shell Chemical Company, under the trademark "Kraton," have the properties required for use in conventional molding equipment and are preferred. Acrylonitrile-butadiene-styrene co-polymer may also be used in the practice of this invention.

Many rubbers and plastics can be vulcanized or molded to form elastomers to provide the base material for the cups of this invention. Many of these are listed in the Encyclopedia of Chemical Technology by Kirk and Othmer, Second Edition, (John Wiley), New York, N.Y., in the herein previously cited patent, in the Handbook of Common Polymers by Scott and Roff, C.R.C. Press, 1971, and in the Plastic Engineering Handbook, Fourth Edition, (Van Nostrand-Reinhold), New York, N.Y.

There are many water-soluble polymers or resin; and new ones, with equivalent properties, are becoming available as a result of the continuing research in this area. The many natural water-soluble resins of vegetable (e.g., starch) and animal (e.g., casein) origin are not preferred, because they are subject to attack by bacteria, are variable in properties, and often contain considerable soluble calcium ions which interfere with the reactivity of the fluoride ions. The synthetic water-soluble polymers or resins are usually either chemically modified compounds with a water-soluble backbone (e.g., cellulose derivatives) or a backbone formed by polymerization of monomers. Among these are: polyacrylic acid, polyvinyl pyrrolidine, polyacrylamide, carboxypolymethylene, poly (ethylene oxide), maleic co-polymers, polyvinyl alcohol, polysaccharides, and others which may be found in the above-mentioned references.

Production of suitable cups in accordance with the present invention may advantageously be carried out by a die cutting operation when natural or synthetic rubber is employed. Preferably, however, an injection molding procedure is utilized with the preferred butadiene-styrene block co-polymer plastic material.

Characteristic of plastic molding procedures are precautions to assure sufficient heating to obtain proper flow properties and conversely, to avoid overheating to prevent charring. Thus, some multiple compositions, especially natural resins, will char before they are fluid enough to be moldable. The molding temperature range must be carefully controlled to balance these effects. Such molding procedures are also well known in the art.

This control of the temperature is even more necessary with plastic compositions containing water-soluble polymers since the latter will inherently char at relatively low temperatures. For example, cellulose will char at usual molding temperatures and compositions containing hydroxypropyl cellulose should not be heated above 330° F.

For injection molding of butadiene-styrene block copolymers, the temperatures required are such that it is preferred to employ thermoplastic water-soluble polymers from the group of hydroxypropyl cellulose, carboxyvinyl polymers, resinous polyethylene oxide, waxy polyethylene glycol ester, polyethylene glycols, polyvinyl alcohol and hydroxypropyl starch.

Hydroxypropyl cellulose water-soluble thermoplastic polymers, such as those manufactured and sold by Hercules, Inc., under the trademark "Klucel" are preferred. These polymers are described as cellulose ethers containing propylene oxide groups attached by ether linkages. The physical properties are determined primarily by the average number of propylene oxide molecules combined per anhydroglucose unit, designated as the "mean substitution" and abbreviated as "m.s.", as is well known in the art. Molecular weights of these polymers range between 60,000 and 1,000,000. Especially preferred are hydroxypropyl cellulose polymers having an m.s. between two and ten.

and preferably an m.s. between 3 and 4.5 with a molecular weight of about 60,000 to 300,000.

Molecular sieves are crystalline zeolites, i.e., silicoaluminates, either natural or synthetic, which have been caused to precipitate in crystal forms with definite structures which permit the passage of units, e.g., molecules or ions, or specific sizes and/or electrical charge characteristics. These structures can be varied by changing the conditions of precipitation. They are characterized by an intercrystalline void and uniform pore diameter and absorbed cations, as well as a crystal type structure which generally is cubic. I prefer cubic molecular sieves in which the pore diameter is from about 3 to 13 A and the void volume is from about 45 to 55 percent. The absorbed cation is Na or K (alkali metal ion) or hydrogen, the pore volume is from about 0.10 to 0.4cc/g., and the density is from about 33 to 45 lbs. per cubic foot. Types A, X and Y have been used successfully. Especially preferred are the molecular sieves manufactured and sold by the Union Carbide Corp., and in particular the molecular sieve sold by Union Carbide Corp. under the designation "4A".

A wide range of fluoride containing anticariogenic agents have been reported in the literature and many of them are compatible for incorporation into the resilient body of the prophy cup. They are all water-soluble and release substantial amounts of fluoride ions for reaction with the tooth enamel. Suitable agents include fluoride and/or stannous ions containing materials soluble in saliva, water or the hydroxy-polar liquids forming the base of the paste used during such treatments. I prefer agents which include one or more water-soluble fluoride salts, such as $SnF_2$, NaF, $InZrF_7$, $AlF_3.H_2O$, $InF_3.H_2O$, $TiF_4$, $ZrF_4$ and amine fluorides, and of these the stannous ion containing fluoride salts are preferred. These and many others are well known in the prior art.

While up to 30 percent (by weight) of the unitary body of the prophy cup is the range of the anticariogenic agent, best results are achieved where at least 10 to 20 percent of the agent is employed.

The polishing and cleaning constitutent of the prophy cup may be up to 50 percent (by weight) of the prophy cup, but best results are achieved where the abrasive is at least about 5 to 10 percent and up to 25 percent.

Other additives besides the usual abrasives may be incorporated as binders, plasticizers and strengtheners in accordance with the practice in the molding art.

It is believed, that the breakdown of the cup by friction and heat generated in the prophylaxis is greatly increased by the dissolution of the water-soluble resins in the saliva.

As the cup is used, the cup breaks down mechanically and chemically. Mechanically it tends to flare outwardly, to be under centrifugal stresses due to its speed of rotation and the "grinding wheel" effect as it works against the teeth. Also, chemically the water-soluble part of the cup is dissolves. As The water-soluble part of the cup dissolves, the heavy metals and fluoride ions from the anticariogenic agents become readily available in effective concentration for contact with the tooth enamel.

The molecular sieve, i.e., the crystalline zeolite, appears to perform three functions. First, it absorbs water; bringing water into the cup to further the breakdown of the cup by dissolving the water-soluble polymer and anticariogenic agents. Second, the calcium ions from the calcium impurities (the calcium in the water, in the paste, or in the abraded tooth enamel, for example) which are in the oral cavity, exchange for the sodium, potassium, or hydrogen in the sieve, the latter going into the solution with no deleterious effect. Third, the catalytic sites in the sieve, it appears, enhance the reactivity of the tin and fluoride ions with the enamel.

While the invention may be practiced with the omission of either the water-soluble polymers or the molecular sieve, it is preferable to use both. When using both, each component has a synergistic effect on the permanent incorporation of fluoride in the tooth enamel. As the anticariogenic fluoride agent, it is preferred to use a combination of NaF and $SnF_2$ (since this results in high fluoride release at a pH in the range for best effect on the tooth enamel), for example, at a pH of about 3.5 to 5. A combination of 0.5 to 15 percent NaF and up to 25 percent $SnF_2$ is preferred.

It is preferred to use a hydroxypropyl cellulose with a mean substitution between 2 and 10 and more preferably from 3 to 4.5, such as Klucel JF sold by Hercules, Inc., since it has been found to be readily compatible with thermoplastic elastomers and to have the desired characteristics of softening the cup and releasing the fluoride in the aqueous systems. Further, a styrene-butadiene-styrene block co-polymer, such as the Kraton 2104 or Kraton 2109 grades sold by the Shell Chemical Company is preferred as the resilient base, because of its strength, elasticity, toughness, and chemical resistance, as well as its excellent injection molding properties.

The preferred general composition for the prophy cup, by weight, is as follows:

| | |
|---|---|
| Water-soluble polymer | 0 to 25 per cent |
| Silico-aluminate zeolite (type A, X, or Y molecular sieve) | 0 to 15 per cent |
| Fluoride | 2.5 to 25 per cent |
| Dental cleaning and polishing agent (abrasive) | 0 to 50 per cent |
| Strengtheners | 0 to 10 per cent |
| Binder | 0 to 7 per cent |
| Plasticizer | 0 to 7 per cent | it being understood that the remainder is the resilient base material, but it is preferred that the resilient base material be not less than 45 percent and not more than 85 percent in any composition.

The preferred specific compositions, by weight, for 10 exemplary cups, designated 3 to 12, inclusive, are given hereafter in Tables I-A and I-B. Tables I-C-1 and I-C-2 which also follow give further additional cup formulations.

TABLE I-A

| | | FORMULATIONS OF EXEMPLARY CUPS | | | | | |
|---|---|---|---|---|---|---|---|
| Ingredients | | 1 | 2 | 3 | 4 | 5 | 6 |
| Resilient Base Material | Kraton 2109 | 82.0 | 73.5 | 58.2 | 58.2 | 58.2 | 62.6 |
| Water-Soluble Polymer | Klucel JF | — | — | 7.8 | — | — | — |
| | Carbowax 4000 | — | — | — | 7.8 | — | 8.4 |
| | Polyox WSR 205 | — | — | — | — | 7.8 | — |
| Molecular Sieve | 4A Sieve | — | — | 10.0 | 10.0 | 10.0 | 5.0 |
| Anticariogenic Agent | NaF | 13.0 | 6.5 | 6.6 | 6.6 | 6.6 | 6.6 |

TABLE I-A-continued

| | FORMULATIONS OF EXEMPLARY CUPS | | | | | | |
|---|---|---|---|---|---|---|---|
| | Ingredients | 1 | 2 | 3 | 4 | 5 | 6 |
| Abrasive | $SnF_2$ | — | — | 12.4 | 12.4 | 12.4 | 12.4 |
| | $Al_2O_3SiO_2$ | — | — | — | — | — | — |
| | Fumed Silica | — | — | — | — | — | — |
| | $ZrSiO_4/Al_2O_3$ | — | 15.0 | — | — | — | — |
| Strengthener | Polystyrene | — | — | — | — | — | — |
| Plasticizer | Mineral Oil | 5.0 | 5.0 | 5.0 | 5.0 | 5.0 | 5.0 |
| | Triacetin | — | — | — | — | — | — |

TABLE I-B

| | FORMULATIONS OF EXEMPLARY CUPS | | | | | | |
|---|---|---|---|---|---|---|---|
| | Ingredients | 7 | 8 | 9 | 10 | 11 | 12 |
| Resilient Base Material | Kraton 2109 | 66.8 | 54.3 | 55.4 | 50.5 | 55.9 | 55.9 |
| Water-Soluble Polymer | Klucel JF | 14.6 | 24.7 | 14.4 | 13.6 | 6.7 | 6.7 |
| | Carbowax 4000 | — | — | — | — | — | — |
| | Polyox WSR 205 | — | — | — | — | — | — |
| Molecular Sieve | 4A Sieve | — | — | — | 5.1 | 13.3 | 13.3 |
| Anticariogenic Agent | NaF | 6.4 | 6.4 | 9.4 | 8.9 | 11.6 | 5.8 |
| | $SnF_2$ | — | — | 17.3 | 16.4 | — | 5.8 |
| Abrasive | $Al_2O_3SiO_2$ | 7.8 | 7.9 | — | — | — | — |
| | Fumed Silica | 0.5 | 1.0 | — | — | — | — |
| | $ZrSiO_4/Al_2O_3$ | — | — | — | — | — | — |
| Strengthener | Polystyrene | — | — | 2.2 | 4.1 | 5.6 | 5.6 |
| Plasticizer | Mineral Oil | 3.9 | 5.7 | — | — | 6.9 | 6.9 |
| | Triacetin | — | — | 1.3 | 1.4 | — | — |

TABLE I-C-1

| | ADDITIONAL CUP FORMULATIONS | | | | | | | | |
|---|---|---|---|---|---|---|---|---|---|
| | Ingredients | 3A | 4A | 5A | 6A | 7A | 8A | 9A | 10A |
| Resilient Base Material | Kraton 2109 | 63.5 | 72.0 | 62.0 | 62.0 | 55.0 | 50.0 | 52.0 | 52.0 |
| Water-Soluble Polymer | Klucel JF | 10.0 | 10.0 | 7.0 | 7.0 | 14.0 | 14.0 | — | — |
| | Carbowax 4000 | — | — | — | — | — | — | 7.0 | — |
| | Polyox | — | — | — | — | — | — | — | 7.0 |
| Molecular Sieve | 4A Sieve | — | — | 13.0 | 13.0 | — | 5.0 | 10.0 | 10.0 |
| Anticariogenic Agent | NaF | 6.5 | 6.5 | 13.0 | 6.5 | 9.0 | 9.0 | 9.0 | 9.0 |
| | $SnF_2$ | — | 6.5 | — | 6.5 | 17.0 | 17.0 | 17.0 | 17.0 |
| Abrasive | $ZrSiO_4/Al_2O_3$ (3:1 wt mixture) | 15.0 | — | — | — | — | — | — | — |
| Strengthener | Polystyrene | — | — | — | — | — | — | — | — |
| Plasticizer | Mineral Oil | 5.0 | 5.0 | 5.0 | 5.0 | 5.0 | 5.0 | 5.0 | 5.0 |
| | Triacetin | — | — | — | — | — | — | — | — |

TABLE I-C-2

| | ADDITIONAL CUP FORMULATIONS | | | | | | | |
|---|---|---|---|---|---|---|---|---|
| | Ingredients | 11A | 12A | 13A | 14A | 15A | 16A | 17A |
| Resilient Base Material | Kraton 2109 | 47.0 | 47.0 | 47.0 | 47.0 | 47.0 | 50.0 | 49.5 |
| Water-Soluble Polymer | Klucel KF | 7.0 | 7.0 | 7.0 | 7.0 | 7.0 | 14.0 | 25.0 |
| Molecular Sieve | 4A Sieve | 5.0 | 5.0 | 5.0 | 5.0 | 5.0 | 5.0 | 5.0 |
| Anticariogenic Agent | NaF | 6.5 | 6.5 | 6.5 | 6.5 | 6.5 | 9.0 | 6.5 |
| | $SnF_2$ | 6.5 | 6.5 | 6.5 | 6.5 | 6.5 | 17.0 | — |
| Abrasive | $Al_3(SiO_4)O$ | 14.0 | — | — | — | — | — | 8.0 |
| | Fumed Silica | — | — | — | — | — | — | 1.0 |
| | Pumice | — | 14.0 | — | — | — | — | — |
| | Mica | — | — | 14.0 | — | — | — | — |
| | $SiO_2$ | — | — | — | 14.0 | — | — | — |
| | Feldspar | — | — | — | — | 14.0 | — | — |
| Strengthener | Polystyrene | 9.0 | 9.0 | 9.0 | 9.0 | 9.0 | — | — |
| Plasticizer | Mineral Oil | 5.0 | 5.0 | 5.0 | 5.0 | 5.0 | — | 5.0 |
| | Triacetin | — | — | — | — | — | 5.0 | — |

Referring to the foregoing tables the resilient base material is a styrene-butadiene-styrene block copolymer sold by the Shell Chemical Co. under the trademark Kraton 2109. The water-soluble polymers are a hydroxypropyl cellulose sold by Hercules, Inc. under the trademark Klucel JF and a waxy polyethylene glycol sold by the Union Carbide Corporation under the trademark Carbowax 4000. Polyoxy (sold by the Union Carbide Corporation) is a high molecular weight (100,000 to 5 million) polymer of ethylene oxide, the particular grade used being designated "Polyox WSR 205". The molecular sieve is a silico-aluminate of type A and is sold by the Union Carbide Corporation under the trademark 4A. The anticariogenic agents are sodium fluoride and tin fluoride. Polystyrene is used as a strengthener. The mineral oil and triacetin are plasticizers. The abrasives are mullite ($Al_2O_3.SiO_2$), zirconium silicate/alumina (3:1 mixture by weight) and fumed silica (the latter sold by the Cabot Corp. under the trademark Cabosil).

The use of these fluoride cups in a prophylaxis will cause a substantial uptake of fluoride into the enamel lattice, i.e., permanent incorporation into the calcium phosphate-apatite crystals, both in the presence and absence of fluoridated prophylaxis pastes. The breakdown of the cups during the prophylaxis from the dissolution of the water-soluble polymer causes a constant release of F and Sn throughout the prophylaxis. This is a significant improvement over present prophy cups.

The uptake of fluoride by the tooth enamel requires energy, because of the thermodynamics of the substitution reaction. The increased surface temperature from the friction resulting from the use of the cups in the prophylaxis, encourages permanent fluoride uptake.

To illustrate the interrelated importance of the water-soluble polymer, molecular sieve, and anticariogenic agent in the prophy cup upon fluoride released during a 10 second treatment period and the subsequent effect upon the permanent enamel fluoride content, Table I-D shows the following:

1. Water soluble polymer is required to allow significant amounts of fluoride to be released from the prophy cup.
2. A combination of NaF and $SnF_2$ increases enamel fluoride content when used with Klucel.
3. Molecular sieve and NaF with Klucel only slightly increases enamel fluoride content.
4. When the NaF to $SnF_2$ ratio is about 9:17 (i.e., 3 percent F from NaF and 3 percent from $SnF_2$) the enamel fluoride content is further increased.

While the exact amount of enamel fluoride uptake that is required to reduce dental caries is not certainly known, significant reductions in dental caries have been reported in association with uptakes of 300 ppm F. Thus, an increase in the permanent fluoride content of the enamel surface of 400 ppm fluoride or more resulting from the use of the prophy cup of this invention suggests significant resistance to dental caries heretofore unattainable using currently available prophylaxis methods and materials. The prior art (i.e., fluoride impregnated prophy cups containing no water soluble thermoplastic polymer or molecular sieve) caused enamel fluoride uptakes of only from 0–150 ppm. This degree of increase is not only statistically insignificant ($p>0.05$) but is of a magnitude to have no apparent effect upon the reduction of dental caries.

A. Enamel Fluoride Uptake

Fluoride uptake by dental enamel (enamel fluoride uptake, abbreviated as "EFU") during a prophylaxis, using a combination of a fluoride containing cup and a paste which may or may not contain a fluoride, is experimentally measured by subjecting bovine enamel sections embedded in plastic blocks to a prophylaxis. The blocks are held in a specially designd apparatus* which controls the rotational speed of the block, the pressure of the cups against the block, the rotational speed of the cup, and the treatment time. The prophy paste is continuously replenished manually during the prophylaxis.

*Mynol, Inc. 600 Parkway, Broomall, Pa. 19008, USA

The bovine sections are first cleaned with a pumice slurry, then etched with 2N $HClO_4$ for 30 seconds and repolished to a high luster with a flour of pumice slurry before being embedded in the blocks. After the prophylaxis, the sections are rinsed and blotted dry. Shields containing windows of 6mm in diameter are placed over the specimens and the open areas are decalcified by immersing each specimen in 5ml of 1.0 N $HCl\ O_4$ for 5 seconds to remove the outer enamel lager (2–4 microns). Aliquots of the acid extract are assayed for the fluoride ions using an Orion Fluoride Specific Electrode and are assayed for the calcium ions using a Perkin-Elmer Atomic Adsorption Spectrophotometer.

The enamel fluoride uptake varies with the depth of enamel penetration so that it is necessary to specify the depth corresponding to a given fluoride uptake. This depth is determined from the calcium removal, by simple calculations from the known area and the relatively constant density and calcium content of the enamel. The uptake in ppm F can be similarly calculated from the density and the amount of F removed.

Deeper layers are removed by de-calcification either for longer times of exposure with 1.0 N $HClO_4$ or by using a stronger concentration of this acid. Ten seconds immersion in 2.0N $HClO_4$ will usually remove enamel to a depth of 8 to 10 microns.

Since enamel, bovine or human, inherently contains fluoride, it is customary to give a prophylaxis using a non-fluoride containing system under identical condi-

TABLE I-D

| Identity | Prophy Cup | | | μg Fluoride Released per 10 sec. treatment | Enamel Fluoride Content | |
|---|---|---|---|---|---|---|
| | Water-Soluble Polymer | Anticariogenic Agent | Molecular Sieve | | 5 micron | 10 micron |
| Conventional Rubber (control) | none | none | none | none | 780 ± 90* | 760 ± 52* |
| Example 1 | none | NaF | none | 1.3 ± 0.6* | 802 ± 78 | 748 ± 25 |
| Example 2 | none | NaF | none | 0.6 ± 0.1 | 820 ± 37 | 786 ± 28 |
| Example 3 | Klucel | NaF/SnF$_2$ | 4A | 44.0 ± 1.8 | 1372 ± 159 | 1185 ± 120 |
| Example 4 | Carbowax | NaF/SnF$_2$ | 4A | 51.4 ± 1.9 | 1082 ± 90 | 850 ± 78 |
| Example 5 | Polyox | NaF/SnF$_2$ | 4A | 29.9 ± 2.6 | 1416 ± 210 | 1278 ± 177 |
| Example 6 | Carbowax | NaF/SnF$_2$ | 4A | 22.8 ± 1.1 | 1365 ± 152 | 1263 ± 152 |
| Example 7 | Klucel | NaF | none | 2.5 ± 0.4 | not measured | |
| Example 9 | Klucel | NaF/SnF$_2$ | none | 22.3 ± 2.8 | 2344 ± 209 | 2158 ± 162 |
| Example 10 | Klucel | NaF/SnF$_2$ | 4A | 11.5 ± 1.6 | 2350 ± 260 | 2171 ± 188 |
| Example 11 | Klucel | NaF | 4A | 2.9 ± 0.4 | not measured | |
| Example 12 | Klucel | NaF/SnF$_2$ | 4A | 15.2 ± 2.9 | not measured | |

*Standard error of the mean, N=12

EXPERIMENTAL EVALUATIONS

The detailed experimental evaluations which follow are not to be construed as limiting this invention.

tions to establish a reference base. The enamel fluoride uptake is defined as the increase in fluoride content of the enamel which is due to the fluoride treatment over the content measured using the reference non-fluoride treatment.

The enamel will ordinarily pick up extra amounts of fluoride loosely held to the surface and not permanently incorporated into the enamel crystals. Therefore, the specimens, before being analyzed for fluoride and calcium, are soaked in a synthetic saliva solution, continuously replenished, for 72 hours and then rinsed clean and blotted dry.

The remarkable effectiveness of the cups produced according to the present invention was demonstrated by a study of the enamel fluoride uptake induced by the cups when applied in a prophylaxis according to the procedure described above. Tables II and III set forth enamel fluoride uptake values resulting from cups made according to the formulations of Examples 3, 4, 5, 6, 9 and 10 in Tables I-A and I-B relative to non-fluoride containing rubber cups at 5 microns ($\mu$) and 10 microns ($\mu$) depth, respectively, and using only a pumice slurry paste. (The data in both Tables II and III are based on the standard error of the mean of 12 replicates.)

Another study was conducted to determine the enamel fluoride uptake when the cups of this invention were used with pastes containing fluoride ions. Tables IV and V summarize the findings when the cups made with formula 3 in Table I-A were used with three conventional fluoride pastes in comparison to a rubber cup. The enamel fluoride uptake measuring procedure previously described was used. The combination of the cups of this invention with fluoride containing pastes produced high enamel fluoride uptake values, as is seen from the results tabulated in Table IV.

TABLE II

| CUP | PASTE | | FLUORIDE CONTENT (PPM) At 5$\mu$ deep | ENAMEL FLUORIDE UPTAKE (PPM) At 5$\mu$ deep |
|---|---|---|---|---|
| Rubber | Pumice | Slurry | (Control) 780 ± 90* | 0 |
| 3 | " | " | 1372 ± 159 | 592 |
| 4 | " | " | 1082 ± 90 | 302 |
| 5 | " | " | 1416 ± 210 | 636 |
| 6 | " | " | 1365 ± 152 | 585 |
| 9 | " | " | 2344 ± 209 | 1564 |
| 10 | " | " | 2350 ± 260 | 1570 |

*Standard error of the mean, N=12

TABLE III

| CUP | PASTE | | FLUORIDE CONTENT (PPM) At 10$\mu$ deep | ENAMEL FLUORIDE UPTAKE (PPM) At 10$\mu$ deep |
|---|---|---|---|---|
| Rubber | Pumice | Slurry | (Control) 760 ± 52* | 0 |
| 3 | " | " | 1185 ± 120 | 425 |
| 4 | " | " | 850 ± 78 | 90 |
| 5 | " | " | 1278 ± 177 | 518 |
| 6 | " | " | 1263 ± 152 | 503 |
| 9 | " | " | 2158 ± 162 | 1398 |
| 10 | " | " | 2171 ± 188 | 1411 |

*Standard error of the mean, N=12

TABLE IV

| CUP | PROPHY PASTE | | FLUORIDE CONTENT (PPM) At 5$\mu$ deep | ENAMEL FLUORIDE UPTAKE (PPM) At 5$\mu$ deep |
|---|---|---|---|---|
| | Abrasive | Fluoride | | |
| Rubber (Control) | Pumice | None | 510 ± 45 | 0 |
| Rubber | $ZrSiO_4$ | $SnF_2$ | 1074 ± 71 | 564 |
| 3 | $ZrSiO_4$ | $SnF_2$ | 1394 ± 184 | 884 |
| Rubber | $SiO_2$ | APF* | 1337 ± 142 | 827 |
| 3 | $SiO_2$ | APF | 1614 ± 188 | 1104 |
| Rubber | Pumice | NaF | 995 ± 82 | 485 |
| 3 | Pumice | NaF | 1429 ± 97 | 919 |

*Combination of $NaF-HF-H_3PO_4$ (acidulated phosphate fluoride)

TABLE V

| CUP | PROPHY PASTE | | FLUORIDE CONTENT (PPM) At 10$\mu$ deep | ENAMEL FLUORIDE UPTAKE (PPM) At 10$\mu$ deep |
|---|---|---|---|---|
| | Abrasive | Fluoride | | |
| Rubber (Control) | Pumice | None | 402 ± 43 | 0 |
| Rubber | $ZrSiO_4$ | $SnF_2$ | 638 ± 51 | 236 |
| 3 | $ZrSiO_4$ | $SnF_2$ | 1210 ± 79 | 808 |
| Rubber | $SiO_2$ | APF* | 1188 ± 102 | 786 |
| 3 | $SiO_2$ | APF | 1385 ± 161 | 983 |
| Rubber | Pumice | NaF | 761 ± 74 | 359 |
| 3 | Pumice | NaF | 1094 ± 77 | 692 |

*Combination of $NaF-HF-H_3PO_4$ (acidulated phosphate fluoride)

B. Enamel Solubility Reduction

An indicator (or yardstick) of the value of some dental enamel treatments is their ability to reduce the solubility of treated tooth enamel when exposed to acidic conditions (pH 3-5) such as are likely to occur in dental plaque. The enamel solubility reduction (abbreviated as "ESR") is ordinarily associated with uptakes of both fluoride and certain heavy metals such as tin. The heavy metal reacts with some of the phosphate in the enamel to produce an amorphous metal phosphate in the surface layer which is more acid resistant than the enamel. Further, the fluoride reacted apatite is in itself more acid resistant.

The cups of this invention, particularly when used with a $SnF_2$ containing prophylaxis paste, are highly effective in enamel solubility reduction by the foregoing mechanisms, measured on bovine enamel sections subjected to a prophylaxis by the procedure cited herein. After the prophylaxis treatments, the sections are shielded and the 6mm windowed specimens are immersed in a 0.2 N acetic acid solution (buffered to pH 4.0) for 5 minutes. The solution is assayed for phosphorous and calcium using an atomic adsorption spectrophotometer. The reference is the amount of these ions dissolved from the bovine enamel section prophied with a non-fluoride and non-tin containing system. The decrease in the amounts of phosphorous and calcium dissolved from the same enamel after prophylaxis with the system containing fluoride and/or tin is the measure of enamel solubility reduction.

The effectiveness of the cups constructed in accordance with this invention is shown in Tables VI and VII which follow and which specify the micrograms ($\mu$g) of phosphorous and calcium, respectively, released. (The data in both Tables VI and VII is based on the standard error of the mean of 12 replicates.)

TABLE VI

| CUP | PASTES | PHOSPHOROUS RELEASED ($\mu$g) | % ENAMEL SOLUBILITY REDUCTION (ESR) |
|---|---|---|---|
| Rubber | Pumice Slurry | 7.97 ± 0.58 | — |
| 3 | Pumice Slurry | 6.61 ± 0.45 | 17.1 |
| Rubber | $SnF_2$-$ZrSiO_4$ | 4.19 ± 0.20 | 47.4 |
| 3 | $SnF_2$-$ZrSiO_4$ | 3.47 ± 0.33 | 56.5 |

TABLE VII

| CUP | PASTES | CALCIUM RELEASED ($\mu$g) | % ENAMEL SOLUBILITY REDUCTION (ESR) |
|---|---|---|---|
| Rubber | Pumice Slurry | 19.9 ± 0.9 | — |
| 3 | Pumice Slurry | 17.2 ± 1.0 | 13.6 |
| Rubber | $SnF_2$-$ZrSiO_4$ | 12.8 ± 0.7 | 35.7 |
| 3 | $SnF_2$-$ZrSiO_4$ | 9.5 ± 0.9 | 52.3 |

C. Constancy of Release

A measure of the constancy or uniformity of fluoride and tin released by the cup throughout its prophy life is shown by a procedure in which the cups are applied against a plastic container using a non-fluoride containing pumice slurry in the special apparatus, permitting controlled prophy conditions. The cup is applied for consecutive ten second intervals after each of which the slurry is washed out and analyzed for fluoride and tin and new slurry introduced.

The uniformity of release, measured in micrograms of fluoride or tin, is shown by the data in Table VIII, testing the formulation 3 cup and based on the standard error of the mean 12 replicates.

TABLE VIII

| USE | $\mu$g RELEASED/10 secs. | |
|---|---|---|
| | Fluoride | Tin |
| After 1 run of 10 secs. | 99.7 ± 6.2 | 153 ± 12 |
| After 14 runs of 10 secs. each | 57.0 ± 6.0 | 65 ± 9 |
| After 28 runs of 10 secs. each | 63.0 ± 7.5 | 68 ± 12 |
| After 48 runs of 10 secs. each | 65.9 ± 7.4 | 61 ± 11 |
| After 56 runs of 10 secs. each | 81.7 ± 5.8 | 88 ± 26 |

D. Increasing the Release of Fluoride

The ability of the hydroxypropyl cellulose (hereinafter referred to as "HPC") to increase the release of fluoride from cups made of resilient material (as compared to prophy cups without it) was demonstrated by blending 10g hydroxypropyl cellulose with 5g NaF and 80g of each of the group of a natural gutta percha rubber, polyethylene, and Hytrel polyester elastomer (sold by duPont). The mixed compositions were in an oven for 30 minutes at 400° F. and then further blended by spatulating. This process was repeated four times to assure homogeneity. Two gram samples of each plastic were then exposed to 25 ml of distilled water for 20 hours at room temperature and the solution analyzed for fluoride ions. The results were compared with samples having no hydroxypropyl cellulose.

TABLE IX

| MATERIAL | % OF TOTAL FLUORIDE RELEASED | |
|---|---|---|
| | Without Hydroxypropyl Cellulose | With Hydroxypropyl Cellulose |
| Natural rubber | 1.8% | 22.2% |
| Polyethylene | 1.5% | 33.9% |
| Hytrel | 2.6% | 20.4% |

The test data in Table IX clearly show that the hydroxypropyl cellulose remarkably increases the release of fluoride, i.e., is a fluoride-releasing agent, when used with a resilient material containing fluoride ions.

SUMMARY

Thus, it is seen that prophy cups incorporating water-soluble polymers and/or a molecular sieve represent a substantial improvement over previous cups, either the conventional rubber cup or one incorporating fluoride ions. The use of this cup will enhance the permanent uptake of fluoride ions into the tooth enamel and make it more resistant to decay. This increased protection is afforded by greater release of fluoride ions in the prophylaxis fluids at the enamel surface and in increased protection from any interfering calcium ions which may be present. Excessive spattering is avoided by the gelatinous character imparted to the paste on the tooth surface by the water-soluble polymer. The cup is sufficiently wear resistant to enable completion of one prophylaxis treatment, yet if flexible, has a good flare and breaks down sufficiently to effect the above improvements in the paste at the surface of the tooth, to significantly increase the permanent fluoride content of tooth enamel, to monitor the pressure and temperature of treatment, and yet the cup is satisfactory for use as a moled snap-on cup or as a screw-on type.

What is claimed is:

1. A dental prophylaxis implement adapted for removable mounting on a dental hand piece and comprising a unitary body formed of resilient material,
said unitary body having an applicator portion for performing a dental prophylaxis,
said resilient material having incorporated therein an anticariogenic agent and a water-soluble polymer, and
means in association with said unitary body for removably mounting the unitary body on the dental hand piece.

2. The combination recited in claim 1 wherein said anticariogenic agent is up to about 30 per cent by weight of said resilient material.

3. The combination recited in claim 1 wherein said water-soluble polymer is up to about 25 percent by weight of said resilient material.

4. The combination recited in claim 1 wherein said resilient material includes a molecular sieve.

5. The combination recited in claim 4 wherein said anticariogenic is up to 30 percent by weight of said resilient material.

6. The combination recited in claim 4 wherein said water-soluble polymer is up to about 25 percent by weight of said resilient material.

7. The combination recited in claim 4 wherein said molecular sieve is up to about 15 percent by weight of said resilient material.

8. The combination recited in claim 5 wherein said polymer is up to 25 percent of said resilient material.

9. The combination recited in claim 8 wherein said molecular sieve is up to 15 percent of said resilient material.

10. The combination recited in claim wherein said anticariogenic agent is up to about 30 percent and said water-soluble polymer is up to about 25 percent by weight of said resilient material.

11. The combination recited in claim 5 wherein said molecular sieve is up to about 15 percent by weight of said resilient material.

12. The combination recited in claim 6 wherein said molecular sieve is up to about 15 percent by weight of said resilient material.

13. The combination of claim 10 wherein said water-soluble polymer is a thermoplastic material selected from the group consisting of hydroxypropyl cellulose and a polyethylene glycol.

14. The combination of claim 3 wherein the water-soluble polymer is hydroxypropyl cellulose.

15. The combination of claim 3 wherein the water-soluble polymer is polyethylene glycol.

16. The combination of claim 10 wherein the anticariogenic agent is selected from the group consistng of NaF and SnF$_2$.

17. The combination of claim 9 wherein said water-soluble polymer is a thermoplastic material selected from the group consisting of hydroxypropyl cellulose and a polyethylene glycol.

18. The combination of claim 11 wherein said water-soluble polymer is a thermoplastic material selected from the group consisting of hydroxypropyl cellulose and a polyethylene glycol.

19. The combination of claim 12 wherein said water-soluble polymer is a thermoplastic material selected from the group consisting of hydroxypropyl cellulose and a polyethylene glycol.

20. The combination of claim 9 wherein said water-soluble polymer is a thermoplastic material selected from the group consisting of hydroxypropyl cellulose and a polyethylene glycol, wherein said anticariogenic agent is selected from the group consisting of NaF and SnF$_2$, and said molecular sieve is a silico-aluminate material.

21. A dental prophylaxis cup comprising a resilient material, an anticariogenic fluoride agent, and a water soluble polymer material.

22. The combination recited in claim 21 wherein said anticariogenic agent is up to about 30 percent by weight.

23. The combination recited in claim 21 wherein said water-soluble polymer is up to about 25 percent by weight.

24. The combination recited in claim 21 and further including a molecular sieve.

25. The combination recited in claim 24 wherein said anticariogenic agent is up to 30 percent by weight.

26. The combination recited in claim 24 wherein said water-soluble polymer is up to about 25 percent by weight.

27. The combination recited in claim 24 wherein said molecular sieve is up to about 15 percent by weight.

28. The combination recited in claim 25 wherein said polymer is up to 25 percent.

29. The combination recited in claim 28 wherein said molecular sieve is up to 15 percent.

30. The combination recited in claim 21 wherein said anticariogenic agent is up to about 30 percent and said water-soluble polymer is up to about 25 percent by weight.

31. The combination recited in claim 25 wherein said molecular sieve is up to about 15 percent by weight.

32. The combination recited in claim 26 wherein said molecular sieve is up to about 15 percent by weight.

33. The combination of claim 20 wherein the molecular sieve is taken from the group consisting of types A, X, and Y.

34. The combination of claim 11 wherein the molecular sieve comprises a silico-aluminate material.

35. The combination of claim 1 wherein the anticariogenic agent comprises a source of fluoride ions.

36. The combination of claim 1 wherein the anticariogenic agent is taken from the group consisting of NaF and SnF$_2$.

37. The combination of claim 1 wherein the resilient material has further incorporated therein up to about 50 percent of a dental cleaning and polishing agent.

38. A dental prophylaxis implement as claimed in claim 1 wherein said unitary body is formed of a styrenebutadiene-styrene block co-polymer and having incorporated therein, by weight, a. up to 25 percent of a cellulose ether containing propylene glycol groups attached by an ether linkage and containing on an anhydrous basis not more than 4.6 hydroxypropyl groups per anhydroglucose unit, b. a molecular sieve which comprises a silico-aluminate material, c. from 2.5 to 10% of fluoride ions as said anticariogenic agent taken from the group of NaF and SnF$_2$, d. up to 10 percent of at least one polymer taken from the group consisting of polyethylene and polystyrene, e. up to 7 percent of a binder and plasticizer, and f. up to 50 percent of a dental cleaning and polishing agent.

39. The combination of claim 1 wherein the composition is, in percent by weight, about:
   63.5% butadiene-styrene block co-polymer,
   10.0% hydroxypropyl cellulose, and
   6.5% NaF
and further includes
   15.0% ZrSiO$_4$/Al$_2$O$_3$ and
   5.0% mineral oil.

40. The combination of claim 1 wherein the composition is, in percent by weight, about:
   72.0% butadiene-styrene block co-polymer,
   10.0% hydroxypropyl cellulose
   6.5% NaF
   6.5% SnF$_2$
and further includes
   5.0% mineral oil.

41. The combination of claim 4 wherein the composition is, in percent by weight, about:
   62.0% butadiene-styrene block co-polymer
   7.0% hydroxylpropyl cellulose,
   13.0% type A silico-aluminate zeolite,
   13.0% NaF
and further includes
   5.0% mineral oil.

42. The combination of claim 4 wherein the composition is, in percent by weight, about:
   62.0% butadiene-styrene block co-polymer,
   7.0% hydroxypropyl cellulose
   13.0% type a silico-aluminate zeolite,
   6.5% NaF and
   6.5% SnF$_2$
and further includes
   5.0% mineral oil.

43. The combination of claim 1 wherein the composition is, in percent by weight, about:
   55.0% butadiene-styrene block co-polymer,
   14.0% hydroxypropyl cellulose
   9.0% NaF and
   17.0% SnF$_2$
and further includes
   5.0% mineral oil.

44. The combination of claim 4 wherein the composition is, in percent by weight, about:
   50.0% butadiene-styrene block co-polymer
   14.0% hydroxypropyl cellulose,
   5.0% type A silico-aluminate zeolite,
   9.0% NaF and
   17.0% SnF$_2$
and further includes
   5.0% mineral oil.

45. The combination of claim 4 wherein the composition is, in percent by weight, about:
   52.0% butadiene-styrene block co-polymer,
   7.0% polyethylene glycol,
   10.0% type A silico-aluminate zeolite, and
   9.0% NaF and
   17.0% SnF$_2$
and further includes
   5.0% mineral oil.

46. The combination of claim 4 wherein the composition is, in percent by weight, about:
   52.0% butadiene-styrene block co-polymer,
   7.0% ethylene oxide polymer,
   10.0% type A silico-aluminate zeolite,
   9.0% type NaF and
   17.0% type SnF$_2$
and further includes
   5.0% mineral oil.

47. The combination of claim 4 wherein the composition is, in percent by weight, about:
   47.0% butadiene-styrene block co-polymer,
   7.0% hydroxypropyl cellulose,
   5.0% type A silico-aluminate zeolite,
   6.5% NaF and
   6.5% SnF$_2$
and further includes
   14.0% Al$_2$(SiO$_4$)O
   9.0% polystyrene, and
   5.0% mineral oil.

48. The combination of claim 4 wherein the composition is, in percent by weight, about:
   47.0% butadiene-styrene block co-polymer,
   7.0% hydroxypropyl cellulose
   5.0% type A silico-aluminate zeolite,
   6.5% NaF and
   6.5% SnF$_2$
and further includes
   14.0% pumice,
   9.0% polystyrene, and
   5.0% mineral oil.

49. The combination of claim 4 wherein the composition is, in percent by weight, about:
   47.0% butadiene-styrene block co-polymer,
   7.0% hydroxypropyl cellulose,
   5.0% type A silico-aluminate zeolite,
   6.5% NaF and
   6.5% SnF$_2$
and further includes
   10.0% mica,
   9.0% polystyrene, and
   5.0% mineral oil.

50. The combination of claim 4 wherein the composition is, in percent by weight, about:
   47.0% butadiene-styrene block co-polymer,
   7.0% polyethylene glycol,
   5.0% type A silico-aluminate zeolite,
   6.5% NaF and
   6.5% SnF$_2$
and further includes
   14.0% SiO$_2$
   9.0% polystyrene, and
   5.0% mineral oil.

51. The combination of claim 4 wherein the composition is, in percent by weight, about:
   47.0% butadiene-styrene block co-polymer,
   7.0% polyethylene glycol,
   5.0% type A silico-aluminate zeolite,
   6.5% NaF and
   6.5% SnF$_2$
and further includes
   14.0% feldspar,
   9.0% polystyrene, and
   5.0% mineral oil.

52. The combination of claim 4 wherein the composition is, in percent by weight, about:
   50.0% butadiene-styrene block co-polymer,
   14.0% hydroxypropyl cellulose,
   5.0% type A silico-aluminate zeolite,
   9.0% NaF and
   17.0% SnF$_2$
and further includes
   5.0% triacetin.

53. The combination of claim 4 wherein the composition is, in percent by weight, about:

49.5% butadiene-styrene block co-polymer,
25.0% hydroxypropyl cellulose, and
5.0% type A silico-aluminate zeolite and
6.5% NaF
and further includes
8.0% $Al_2(SiO_4)O$
1.0% fumed silica, and
5.0% mineral oil.

54. The combination of claim 1 wherein the composition is, in percent by weight, about:
55.4% butadiene-styrene block co-polymer,
14.4% hydroxypropyl cellulose,
9.4% NaF and
17.3% $SnF_2$
and further includes
2.2% polystyrene, and
1.3% triacetin.

55. The combination of claim 4 wherein the composition is, in percent by weight, about:
50.0% butadiene-styrene block co-polymer,
13.7% hydroxypropyl cellulose
8.9% NaF
16.4% $SnF_2$ and
5.0% type A silico-aluminate zeolite,
and further includes
4.1% polystyrene, and
1.4% triacetin.

56. The combination of claim 4 wherein the composition is, in percent by weight, about:
58.2% butadiene-styrene block co-polymer,
7.8% hydroxypropyl cellulose,
10.0% type A silico-aluminate zeolite,
6.6% NaF and
12.4% $SnF_2$
and further includes
5.0% mineral oil.

57. The combination of claim 4 wherein the composition is, in percent by weight, about:
58.2% butadiene-styrene block co-polymer,
7.8% polyethylene,
10.0% type A silico-aluminate zeolite,
6.6% NaF and
12.4% $SnF_2$
and further includes
5.0% mineral oil.

58. The combination of claim 4 wherein the compositin is, in percent by weight, about:
62.6% butadiene-styrene block co-polymer,
8.4% polyethylene glycol,
5.0% type A silico-aluminate zeolite,
6.6% NaF and
12.4% $SnF_2$
and further includes
5.0% mineral oil.

59. The combination of claim 1 wherein the composition is, in percent by weight, about:
54.3% butadiene-styrene block co-polymer,
24.7% hydroxypropyl celllulose, and
6.4% NaF
and further includes
7.9% mullite,
1.0% fumed silica, and
5.7% mineral oil.

60. The combination of claim 4 wherein the composition is, in percent by weight, about:
55.9% butadiene-styrene block co-polymer,
6.7% hydroxypropyl cellulose,
13.3% type A silico-aluminate zeolite,
5.8% NaF and
5.8% $SnF_2$
and further includes
5.6% polystyrene, and
6.9% mineral oil.

* * * * *